(12) United States Patent
Nägele Nacken

(10) Patent No.: US 8,951,227 B2
(45) Date of Patent: Feb. 10, 2015

(54) DEVICE FOR THE ADMINISTRATION OF INJECTABLE PRODUCTS WITH A CONTROLLED FLOW RATE

(75) Inventor: Elisabeth Nägele Nacken, Sta. Cruz de Tenerife (ES)

(73) Assignee: INNOVA Salud Desarrollos Sanitarios, S.L., Madrid (ES)

( * ) Notice: Subject to any disclaimer, the term of this patent is extended or adjusted under 35 U.S.C. 154(b) by 0 days.

(21) Appl. No.: 13/147,179

(22) PCT Filed: Jan. 29, 2010

(86) PCT No.: PCT/ES2010/000033
§ 371 (c)(1),
(2), (4) Date: Oct. 10, 2011

(87) PCT Pub. No.: WO2010/086476
PCT Pub. Date: Aug. 5, 2010

(65) Prior Publication Data
US 2012/0024987 A1    Feb. 2, 2012

(30) Foreign Application Priority Data
Jan. 29, 2009   (ES) .................... 200900255

(51) Int. Cl.
*A61M 37/00*    (2006.01)
*A61M 5/00*     (2006.01)
(Continued)

(52) U.S. Cl.
CPC ............ *A61M 39/24* (2013.01); *A61M 5/2046* (2013.01); *A61M 5/31511* (2013.01);
(Continued)

(58) Field of Classification Search
CPC ............ A61M 1/0058; A61M 1/0031; A61M 2205/3331; A61M 2205/12; A61F 9/00736

USPC ............... 604/30–34, 65–67, 167.03–167.06, 604/168.01, 131, 246
See application file for complete search history.

(56) References Cited

U.S. PATENT DOCUMENTS

| 4,475,906 A | 10/1984 | Holzner |
| 6,099,505 A | 8/2000 | Ryan |
| 6,120,478 A | 9/2000 | Moore et al. |
| 6,520,939 B2 | 2/2003 | Lafontaine |
| 2001/0049501 A1 | 12/2001 | Osbourne et al. |
| 2007/0225648 A1* | 9/2007 | Winsor et al. ............ 604/167.04 |

FOREIGN PATENT DOCUMENTS

| DE | 31 06 382 | 1/1982 |
| EP | 0 077 779 | 11/1986 |

(Continued)

OTHER PUBLICATIONS

International Search Report for International Application No. PCT/ES2010/000033 mailed Jul. 2, 2010.

*Primary Examiner* — Theodore Stigell
*Assistant Examiner* — Pritesh Patel
(74) *Attorney, Agent, or Firm* — Merchant & Gould P.C.

(57) ABSTRACT

A device is for the administration of injectable products with controlled flow rate, with a container (23) in the form of both a syringe and an ampoule preloaded with the injectable product, an injection port (25) and a control valve (21) for controlling the outlet rate and pressure arranged between the injectable products and the injection port (25). A device for reducing the outlet flow rate depends on the pressure increase applied during the administration of the injectable product, the administration being moderated by closing the valve (21) when the pressure exceeds a predetermined limit. A device prevents the backflow of fluids during the administration of the injectable product. The valve (21) can be positioned both in the container (23) and at an injection end (27) including the injection port (25) which is coupled to the container (23).

2 Claims, 2 Drawing Sheets

(51) Int. Cl.
*A61M 39/24* (2006.01)
*A61M 5/20* (2006.01)
*A61M 5/315* (2006.01)
*A61M 5/31* (2006.01)
*A61M 5/168* (2006.01)

(52) U.S. Cl.
CPC ................. *A61M 2005/3128* (2013.01); *A61M 2039/2413* (2013.01); *A61M 2039/244* (2013.01); *A61M 5/16813* (2013.01); *A61M 2039/248* (2013.01); *A61M 2039/2486* (2013.01)
USPC .......................................... 604/131; 604/246

(56) References Cited

FOREIGN PATENT DOCUMENTS

| | | |
|---|---|---|
| ES | 380814 | 4/1973 |
| ES | 2 280 398 | 9/2007 |
| GB | 1 327 024 | 8/1973 |
| WO | WO 82/03777 | 11/1982 |
| WO | WO 93/09826 | 5/1993 |
| WO | WO 93/19793 | 10/1993 |
| WO | WO 00/40291 | 7/2000 |
| WO | WO 01/00261 | 1/2001 |
| WO | WO 03/002182 | 1/2003 |

* cited by examiner

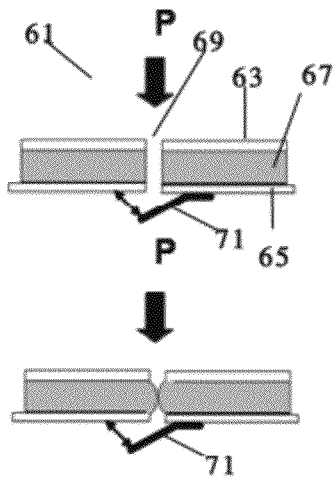
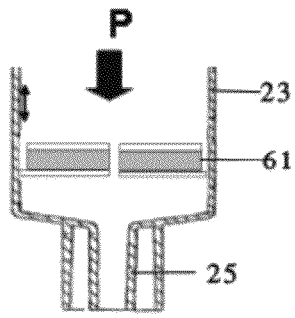
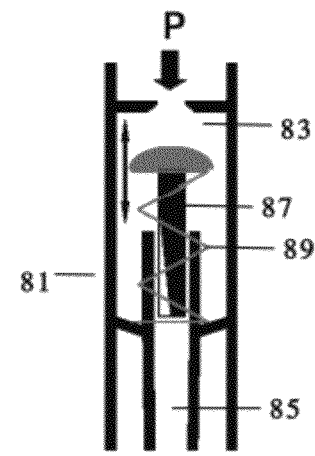
FIG. 4a
FIG. 4b
FIG. 5a
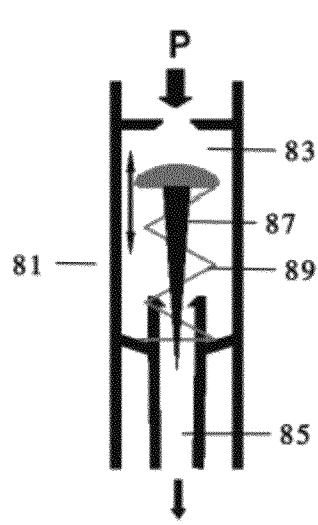
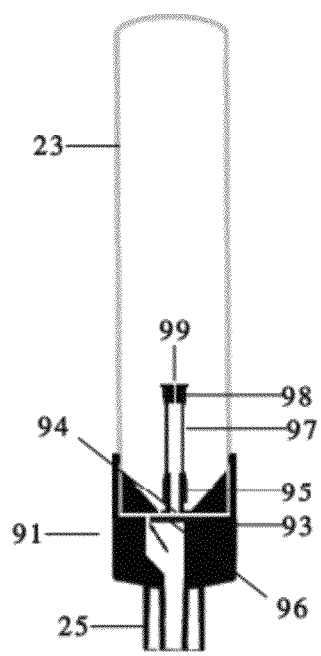
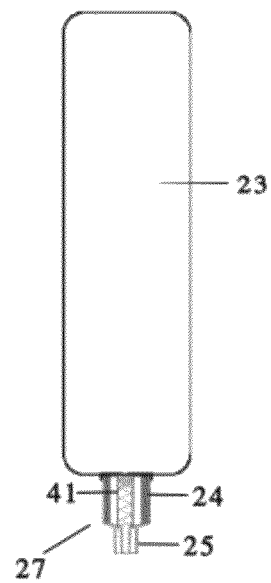
FIG. 5b
FIG. 6
FIG. 7

DEVICE FOR THE ADMINISTRATION OF INJECTABLE PRODUCTS WITH A CONTROLLED FLOW RATE

This application is a National Stage Application of PCT/ES2010/0000333, filed 29 Jan. 2010, which claims benefit of Ser. No. P200900255, filed 29 Jan. 2009 in Spain and which applications are incorporated herein by reference. To the extent appropriate, a claim of priority is made to each of the above disclosed applications.

FIELD OF THE INVENTION

The present invention relates to a device for the administration or dosing of injectable products, and more particularly to a device which allows controlling the injected flow rate.

BACKGROUND OF THE INVENTION

Current injection devices are generally syringe-type devices, i.e., with a plunger which is moved inside a cylinder and expels the content through one end, where the needle for injecting the liquid into the patient can be connected, or it can be connected to systems previously implanted in the patient, such as catheters.

The injection flow rate is controlled by the speed of movement of the plunger, and such speed is controlled by trained and experienced healthcare personnel. Excessive flow rate can cause adverse effects in the patient such as broken veins, extravasations, etc. The same occurs with an excessive outlet pressure.

With syringe-type injection devices, injectable products must be administered by healthcare professionals except in the case of some small-volume intramuscular injections, such as some vaccines, or in the case of diabetics self-injecting insulin.

The presence of a healthcare professional is also necessary when injection devices in which there may be backflow of biological fluids, or a return of these fluids through the needle or system implanted in the patient, especially blood in the case of intravenous injections, are used.

Furthermore, the use of syringe-type injection devices generally involves the use of both hands, one for holding the cylinder or body and the other for moving the plunger, and this also makes the presence of a healthcare professional necessary to prevent unsuitable movements of the syringe which may hurt the patient.

Given the scarcity and the cost of healthcare professionals, there is a need for injection devices which can be used risk-free by non-specialized personnel.

The use of preloaded injection devices for facilitating the administration of injectable products to patients is well known. Different proposals are known in this sense, and in relation to ampoule-type proposals, those described in patents U.S. Pat. Nos. 4,475,906, 6,120,478, WO 93/09826, EP 0 077 779 and DE 3106382 can be cited. However, other than in exceptional cases, the preloaded injection devices known by the applicant must be used by healthcare professionals.

A similar drawback arises in the control of dosing products requiring delicate handling, such as corrosives or reagents in research laboratories and in other industrial sectors.

The present invention aims to solve these drawbacks.

SUMMARY OF THE INVENTION

An object of the present invention is to provide an injection device preloaded with a pharmaceutical product injectable into patients which does not require being handled by a healthcare professional.

Another object of the present invention is to provide an easy-to-use and low-cost injection device preloaded with a pharmaceutical product injectable into patients.

Another object of the present invention is to provide a dosing device preloaded with a liquid product which requires a controlled dosing either in research laboratories or in other industrial sectors.

These and other objects are achieved with a device for the administration or dosing of an injectable product comprising a container preloaded with the injectable product and an injection port as well as a control valve for controlling the outlet flow rate and pressure arranged between the injectable product and the injection port, and provided with means for varying the outlet flow rate depending on the pressure applied during the administration of the injectable product, reducing the flow rate increase with respect to the pressure increase.

In a preferred embodiment of the present invention, said device is formed in a single part. A particularly useful injection device is thereby obtained for facilitating the administration of injectable products by non-specialized personnel.

In another preferred embodiment of the present invention said device is formed in separate parts provided for being connected to one another when the injectable product is to be administered. An injection device is thereby obtained which facilitates the use of preloaded injectable products.

In another preferred embodiment said device also comprises means preventing the backflow of fluids towards said container during the administration of the injectable product. An easy-to-use and low-cost injection device which is suitable for intravenous injections is thereby obtained.

In another preferred embodiment the injectable product container is made of an elastic material which transmits the pressure exerted on the outer surface of the container on the injectable product. A particularly useful injection device is thereby obtained for facilitating the administration of injectable products by non-specialized personnel.

Other features and advantages of the present invention will be inferred from the following detailed description of an illustrative embodiment of its object in relation to the attached drawings.

DESCRIPTION OF THE DRAWINGS

FIG. 4a shows schematic cross-section views of a valve that can be applied to an injection device according to another embodiment of the present invention and FIG. 4b schematically shows a partial cross-section view of an injection device with said valve.

FIGS. 5a and 5b show schematic cross-section views of a valve that can be applied to an injection device according to another embodiment of the present invention.

FIG. 6 schematically shows a cross-section view of an injection device according to another embodiment of the present invention with a control valve inside it.

FIG. 7 schematically shows a partial cross-section view of an injection device formed by an injectable liquid container in the form of an ampoule and an injection end.

DETAILED DESCRIPTION OF THE INVENTION

The basic idea of the present invention is to provide an injection device with a control valve for controlling the outlet flow rate of the injectable product depending on the pressure applied to the injectable product.

Figure 1:
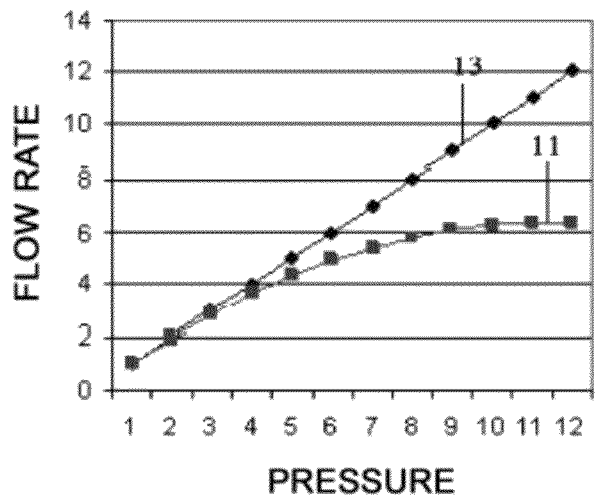
FIG. 1 shows the pressure-flow rate curve in a conventional injection device and in an injection device according to the present invention.

As is well known, at a given application pressure for the injectable product, the outlet flow rate (and therefore the outlet pressure) in an injection device depends on the surface of the outlet opening. At an equal application pressure, the flow rate will be less the smaller the surface of the opening. However, since the application pressure in the administration of injectable products is not usually constant, it is necessary to act on the outlet surface if the outlet pressure or flow rate is to be controlled. As the application pressure increases, the surface of the outlet opening S must be reduced so that the outlet flow rate is not greater than what is considered safe. If there were a small fixed surface S implying a small flow rate even under high application pressures, the flow rate under a low pressure would be as small as the application time would be excessive. Therefore, with low pressures, the surface S must be high such that it assures a high flow rate, and therefore a normal application time. As the pressure goes up, the flow rate must increase but in a moderated manner and in any case it cannot increase the maximum safety flow rate. This is graphically depicted in FIG. 1 where line 11 depicts the application pressure—outlet flow rate graph in an injection device according to the invention and line 13 depicts the same graph in a conventional injection device.

In the particular case of an injection device according to the present invention aimed at the administration of pharmaceutical products to patients, it should be said that it comprises at least the following elements:

A container 23 housing a preloaded injectable product with means which allow applying pressure on the injectable product.

An injection port 25 with means for coupling to the needle or catheter used to administer the injectable product to the patient.

A valve 21 which allows regulating the outlet flow rate of the injectable product towards the injection port 25 depending on the pressure applied on the injectable product contained in said container 23, even closing the valve if the applied pressure exceeds a pre-established threshold. The valve 21 can be positioned both in the container containing 23 the injectable product and at an injection end including the injection port 25.

Said device can be formed in a single part or in separate parts provided for being connected to one another when the injectable product is to be administered. Where appropriate, and as will be understood by the person skilled in the art, the injection device will additionally include any suitable means of those known in the art for assuring sterility and safety.

The injectable product container 23 can be both a syringe-type container and a gravity drip container or a plastic ampoule. In turn, the injectable product can be administered by people who are neither trained nor experienced. The implantation of injection means in the patient, such as catheters, always requires the presence of a professional, but not the subsequent injection. Home nursing care or care in places where there are few professionals can thereby be given with a high degree of safety.

The valve 21 of the present invention has limiting means for limiting the injectable product outlet flow rate, which limit the flow rate to a pre-established maximum value, which could even be nil, when the pressure increases up to a predetermined value. These limiting means for limiting the flow rate are formed by at least one passage opening 29 for the passage of injectable product which can gradually be blocked by blocking means that are operated by the effect of the pressure of the injectable product, limiting the passage of the injectable product through the opening 29 to a pre-established maximum value when the pressure predetermined value.

Figure 2A:
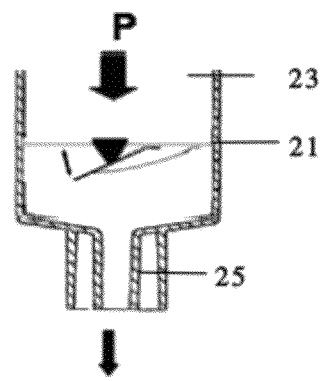
FIG. 2a schematically shows a partial cross-section view of an injection device according to an embodiment of the present invention with a control valve inside it.
Figure 2B:
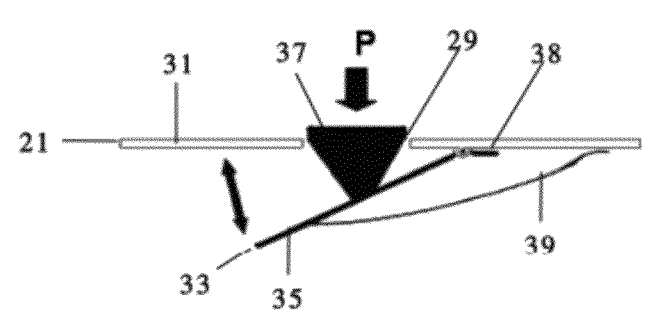
FIG. 2b shows an enlarged view of said valve.

Now describing the preferred embodiments of the invention, following FIGS. 2a and 2b, the part of an injection device according to the present invention comprising an injection port 25 and a control valve 21 can be observed. That device graphically corresponds with a syringe-type device in which the control valve 21 is placed in the lower part of a container 23 and in which a plunger (not depicted) applies pressure P to the injectable product. For the purpose of the present invention, the device shown in FIG. 2a can also correspond to an injection end that can be coupled to, for example, a plastic ampoule acting as a container for the injectable product, P being the pressure resulting from applying pressure on the walls of the ampoule.

The valve 21 comprises a plate-shaped valve body 31 fixed to the inner walls of the container 23 with a passage opening 29 for the passage of the injectable product that can be blocked by the means. The blocking means are formed by a plate 35 arranged on the lower face of the valve body 31 which moves to open the passage opening operated by a block 37 which is in turn operated by the effect of the pressure of the injectable product. To block the passage opening 29, the plate 35 moves in the opposite direction operated by a spring 39 fixed to the plate and attached in an articulated manner to the lower face of the valve body 31. Given the configuration of the block 37, it blocks; the opening 29 in a magnitude proportional to the pressure P applied to the injectable liquid up to a particular threshold assured by the configuration of the plate 35 and a stop 38 arranged at the fixing point for fixing the plate 35 to the valve body 31. If the opening 29 is circular, a suitable configuration of the block 37 is the inverted conical configuration illustrated in FIGS. 2a and 2b.

Figure 3A:
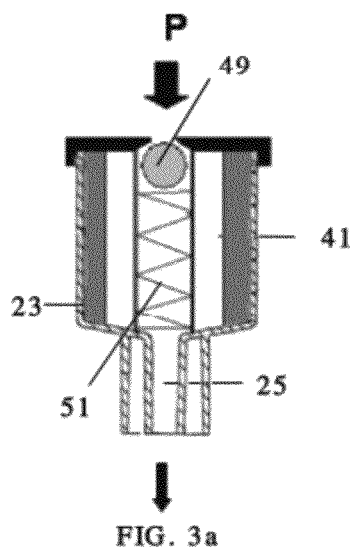
FIG. 3a schematically shows a cross-section view of an injection device according to another embodiment of the present invention with a control valve inside it.
Figure 3B:
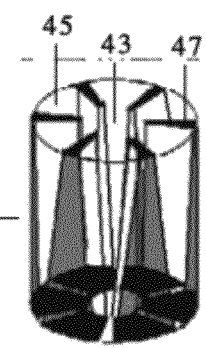
FIG. 3b shows a schematic perspective view of said valve.
Figure 3C:
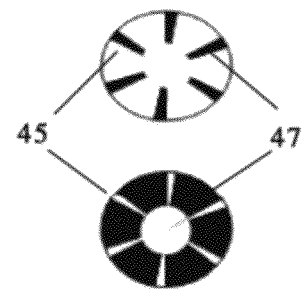
FIG. 3c shows top and bottom plan views of said valve.

In another embodiment of the invention illustrated in FIGS. 3a, 3b and 3c, the injection device comprises a cylindrical-shaped valve body 41 with a central hollow 29 acting as the passage opening for the passage of the injectable product and a plurality of inner peripheral hollow areas 45 of decreasing section in the direction of the outlet surface, connected with the central hollow 29 and demarcated by radial fins 47 made of a rigid material which, in a preferred embodiment, can be the same material with which the container 23 is made. The blocking means for blocking the central hollow 29 of the valve 21 comprise a spherical blocking element 49 arranged in said central hollow 29.

The spherical blocking element 49 moves throughout the central hollow 29 in the outlet direction by the effect of the pressure of the injectable product and it moves in the direction opposite the outlet operated by a cylindrical spring 51 arranged inside the central hollow 29. The blocking element 49 prevents the backflow with low or nil pressure P.

The operation of said valve 21 with a cylindrical shaped valve body 41 can be described as follows: when pressure P is applied, the spherical blocking element 49 moves in the outlet direction, allowing the liquid to surround it through the hollow areas 45. The greater the pressure P, the greater the movement is, reaching the area where the hollow areas 45 have a smaller surface, so the flow rate is moderated. The liquid moves at a greater speed due to the greater pressure, but since the surface is smaller, the total flow rate is less than what it would be if the surface of the hollow areas 45 were the same as in the part close to the inlet opening. With maximum pressure, the blocking element 49 will be in the area close to the outlet, where the surface of the hollow areas 45 is very small, so the flow rate is limited to the maximum allowed for the patient's safety. It could even be zero if the hollow areas 45 disappear in a particular embodiment. The radial fins 47 assure the longitudinal movement of the spherical blocking element 49 throughout the central hollow 29.

In another embodiment of the invention illustrated in FIGS. 4a and 4b, the injection device comprises a valve 21 having a ring-shaped valve body 61 in which the passage opening 29 for the passage of the injectable product is arranged. The ring-shaped valve body 61 is made up of two ring-shaped upper 63 and lower plates 65 made of a rigid material and an intermediate layer 67, arranged between the upper plate 63 and lower plate 65,of an elastic material such as silicone, for example, the size of the central opening 29 and the thickness of the intermediate layer 67 of elastic material are sized such that when pressure P is applied, the outlet surface of the opening central 29 is reduced to a particular limit in a manner similar to the preceding embodiments. The lower plate 65 is larger than the upper plate 63 since it must be fixed to the wall of the container 23, whereas the upper plate 63 must be separated from it in order to be able to move such that with pressure P it compresses and deforms the intermediate layer 67. In this case, the blocking means for blocking the opening 29 have a flap 71 which is attached at one of its ends to the lower plate 65. The flap 71 is made of a semi-flexible material such as a silicone that is more rigid than that used in intermediate layer 67 which, in the rest state, i.e., in absence of pressure, closes the opening 29 and prevents backflow whereas when there is pressure, the liquid bends the flap 71, the later moving and opening the passage opening 29, allowing the passage of said liquid.

In other embodiments of the invention illustrated in FIGS. 5a and 5b, a valve 21 of an injection device comprising an enclosure 83 with an outlet channel 85 acting as a passage opening 29 towards the injection port. In this case, the blocking means for blocking the opening 29 comprise a blocking stopper 87 arranged in the enclosure 83 operated by a spring 89 arranged inside the enclosure 83 and fixed to said blocking stopper 87. The blocking stopper 87 moves to open the opening 29 by the effect of the pressure of the injectable product and moves in the opposite direction to block the opening 29, operated by the spring. As seen in FIGS. 5a and 5b, the blocking stopper 87 is configured to progressively reduce the surface of the outlet opening 29 depending on the pressure P, although the degree of that reduction is different in both cases depending on its specific configuration: in the case of FIG. 5a it allows a considerable reduction of said surface from the initial phase of applying pressure P, whereas in the case of FIG. 5b the reduction of the surface is allowed to take place progressively as the pressure P is increased.

In another embodiment of the invention illustrated in FIG. 6, the control valve 21 comprises a substantially cylindrical-shaped valve body in which the passage opening 29 for the passage of the injectable product towards the injection port 25 is arranged. In this embodiment, the blocking means for the blocking opening 29 have a prolongation towards the inside of the container 23 in the direction opposite the injection port 25, to which there is coupled a tube 97 made of an elastic material such as silicone which can incorporate a stopper 98 with an inlet opening 99 for the injectable product, such that the tube 97 deforms by the effect of the pressure of the injectable liquid, reducing the dimensions of said tube 97 upon increasing the pressure. The blocking means additionally have an elastic flap 71 arranged in the passage opening 29.

The operation of the device can be described as followed: once pressure is applied to the flexible container 23, the injectable product enters the outlet opening 29 through the opening 99 of the stopper 98 of the tube 97 or directly through the tube 97 if it does not incorporate the stopper 98, and the configurations of those elements are provided, as illustrated in FIG. 6, so that in normal operation, the passage opening 29 assures a duly controlled flow rate towards the injection port 25 once the flap 96 is moved by the effect of the pressure. At the same time, an opening 94 also allows the passage of the liquid and moves the flap 71. In the rest state, the flap 71 closes the passage opening 29 and the opening 94 and prevents backflow. If the pressure inside the container 23 is excessive, the tube 97 folds and closes the passage of the injectable product through the opening 99, there remaining only the flow rate passing through the opening 94 the section of which allows the passage of a volume which is sized such that it is less than a predetermined safety volume. Therefore, the function of the opening 94 is to let a minimum liquid pass when the tube 97 has collapsed and therefore it does not let anything pass. The opening 94 could be located directly in the tube of the opening 29 but it is separated to facilitate the manufacture.

The valves 21, include means preventing the backflow of fluids towards the inside of the container 23 the plate 35, and the spring 39 in the embodiment shown in FIGS. 2a and 2b, the assembly of the spherical blocking element 49 and the spring 51 in the embodiment shown in FIGS. 3a, 3b and 3c, the semi-flexibility of the flap 71 in the embodiment showing in FIGS. 4a and 4b, the assembly of the blocking stopper 87, and the spring 89 in the embodiment shown in FIGS. 5a and 5b and the elastic flap 71 in the embodiment shown in FIG. 6. In the rest state, those means assure that the valves 21 are closed and that certain pressure is necessary to open them.

In a preferred embodiment of the present invention illustrated in FIG. 7, the container 23 housing the injectable product is an ampoule made of a flexible plastic such as polyethylene which can contain any injectable liquid that is compatible with the plastic of the ampoule and considering its expiration date. Ampoules of that type can also contain liquids extemporaneously prepared in a suitable location, such as the pharmacy of a hospital, for their application in the hospital or at home. In the embodiment shown in FIG. 7, the injection device uses the valve 21 illustrated in FIGS. 3a, 3b and 3c but, as the person skilled in the art will understand, any of the other valves that have been described can be used.

The port of the injection device can be "Luer Lock" or "Luer Slip". In both cases, this end must be sealed to prevent the outlet of the liquid and contamination. In the case of the "Luer Lock", it can be closed until it is used with a stopper or by sealing using medical-grade paper welded to the outer ring.

If the injection device is not formed in a single part but comprises, in reference to FIG. 7, on one hand an ampoule 23 and on the other hand an injection end 27 with the control valve and the injection port 25, in addition to having the outlet port sealed, it must also have the opposite side, where the independent ampoule (the port of which will also be sealed) will be fitted, and where there will be a needle or suitable equivalent perforating the ampoule and allowing the entrance of the liquid into the injection end, sealed. The securing system can be a screw system or the like.

Each control valve is designed for a maximum pre-established flow rate that can vary depending on the viscosity of the injectable fluid.

The operation of this injection device is as follows: the user compresses the ampoule and the device releases the liquid, automatically controlling the flow rate, without the user needing to have any special training. This facilitates treating patients in their home, preparing medication in a suitable location prior to its administration, as well as administering injectable products in locations where there are no professionals.

The use of ampoules in turn has several advantages: they are inexpensive, easy-to-handle (they are applied with one hand), generate fewer residues, are easier to transport, take up less space for the same volume. The use of injection devices with ampoules without control valves for controlling the flow rate would be problematic for healthcare professionals (who are not trained to control the outflow rate) and non-viable for non-professionals except in very specific cases of small ampoules.

A feature that is common to all the embodiments of the present invention is that under maximum pressure the surface of the outlet opening is not completely reduced such that there is always flow rate, which is the maximum safety flow rate. In other words, the maximum flow rate takes place with maximum pressure and minimum surface of the opening. Nevertheless, the present invention can also be carried out such that when the applied pressure is excessive, the valve completely closes the passage of the liquid.

Those modifications comprised within the scope defined by the following claims can be introduced in the preferred embodiments described above.

The invention claimed is:

1. A device for the administration or dosing of an injectable product comprising:
   a container preloaded with the injectable product and an injection port, and
   a control valve for controlling the outlet flow rate and pressure arranged between the injectable product and the injection port, wherein the valve comprises limiting means for limiting the injectable product outlet flow rate, which limit the flow rate to a pre-established maximum value when the pressure increases up to a predetermined value,
   the limiting means comprising at least one passage opening for the passage of the injectable product which can gradually be blocked by blocking means operable by the effect of the pressure of the injectable product, limiting the passage of the injectable product through the opening to a pre-established maximum value when the pressure increases up to a predetermined value;
   wherein said valve comprises anti-backflow means for preventing backflow of fluids during administration or dosing of the injectable product;
   wherein said control valve comprises an enclosure in which the passage opening for the passage of the injectable product is arranged,
   and wherein the blocking means for blocking said passage outlet comprise a blocking stopper arranged in the enclosure which moves to open the opening by the effect of the pressure of the injectable product, and which moves to block the opening operated by a spring arranged inside the enclosure and fixed to said blocking stopper.

2. A device for the administration or dosing of an injectable product comprising:
   a container preloaded with the injectable product and an injection port, and
   a control valve for controlling an outlet flow rate and pressure arranged between the injectable product and the injection port, wherein the valve comprises limiting means for limiting the injectable product outlet flow rate, which limit the flow rate to a pre-established maximum value when the pressure increases up to a predetermined value,
   the limiting means comprising at least one passage opening for the passage of the injectable product which can gradually be blocked by blocking means operable by the effect of the pressure of the injectable product, limiting the passage of the injectable product through the opening to a pre-established maximum value when the pressure increases up to a predetermined value,
   said control valve comprises a substantially cylindrical-shaped valve body in which the opening is arranged, and an opening for passage of the injectable product towards the injection port and anti-backflow means for preventing backflow of fluids during administration or dosing of the injectable product;
   the blocking means for blocking the opening comprise:
   a prolongation towards an inside of the container in the direction opposite the injection port to which there is coupled a tube made of an elastic material with an inlet opening for the inlet of the injectable product, the tube being deformed by the effect of the pressure of the injectable liquid, reducing the dimensions of said tube upon increasing the pressure,
   and an elastic flap arranged in the passage opening the flap moving to open the passage opening by the effect of the pressure of the injectable product,
   and the flap closing the passage opening in the absence of pressure.

* * * * *